US008306829B2

(12) United States Patent
Starkey et al.

(10) Patent No.: US 8,306,829 B2
(45) Date of Patent: Nov. 6, 2012

(54) METHOD FOR DETERMINING ELIGIBILITY FOR AN ASSISTANCE PROGRAM

(75) Inventors: Judith Edmonds Starkey, Atlanta, GA (US); Kevin Sutherland, Snellville, GA (US)

(73) Assignee: Chamberlin Edmonds & Associates, Atlanta, GA (US)

( * ) Notice: Subject to any disclaimer, the term of this patent is extended or adjusted under 35 U.S.C. 154(b) by 1756 days.

(21) Appl. No.: 09/930,668

(22) Filed: Aug. 15, 2001

(65) Prior Publication Data

US 2003/0036926 A1    Feb. 20, 2003

(51) Int. Cl.
*G06Q 50/00*    (2006.01)
*G06Q 10/00*    (2006.01)
(52) U.S. Cl. .................................. 705/2; 705/322; 705/4
(58) Field of Classification Search .......................... None
See application file for complete search history.

(56) References Cited

U.S. PATENT DOCUMENTS

| | | | |
|---|---|---|---|
| 3,727,190 A | | 4/1973 | Vogelman et al. |
| 4,491,725 A | * | 1/1985 | Pritchard ........................... 705/2 |
| 4,975,840 A | * | 12/1990 | DeTore et al. ..................... 705/4 |
| 5,235,702 A | | 8/1993 | Miller |
| 5,301,105 A | | 4/1994 | Cummings, Jr. |
| 5,359,509 A | | 10/1994 | Little et al. |
| 5,557,514 A | | 9/1996 | Seare et al. |
| 5,583,760 A | * | 12/1996 | Klesse ............................. 705/38 |
| 5,644,778 A | | 7/1997 | Burks et al. |
| 5,704,044 A | | 12/1997 | Tarter et al. |
| 5,803,498 A | * | 9/1998 | Tung et al. ....................... 283/56 |
| 5,832,447 A | | 11/1998 | Rieker et al. |
| 5,930,759 A | | 7/1999 | Moore et al. |
| 2002/0107849 A1 | * | 8/2002 | Hickey et al. .................... 707/3 |

FOREIGN PATENT DOCUMENTS

EP    683465 A2 *  11/1995

OTHER PUBLICATIONS

"IndiCare" Website Users Manual, 1997, pp. 1-17.*
Anonymous, "Recondo Technology Announces Financial Assistance Software Service:—Software service helps hospitals determine patient financial assistance" Oct. 20, 2010, PR Newswire [New York].*

* cited by examiner

*Primary Examiner* — Luke Gilligan
*Assistant Examiner* — Rachel L Porter
(74) *Attorney, Agent, or Firm* — Seyfarth Shaw LLP; Brian L. Michaelis; Joseph M. Walker

(57) ABSTRACT

A system for determining a patient benefits eligibility under a healthcare assistance program. Initial patient information, such as the patient's date of birth, household members, medical condition including pregnancy, and income and financial resources, if available, is used to make an initial determination as to whether the patient is likely to qualify for benefits. If the initial patient information satisfies one of the well-established criteria or the probability models, additional patient information is obtained, typically including additional details about the patient's income and financial resources, as well as the income and financial resources of the patient's household. The patient information is compared to the eligibility requirements for the assistance program. If the comparison indicates that it is likely that the patient will qualify for benefits under the assistance program, then an application for the assistance program is provided and the application is completed and submitted.

30 Claims, 3 Drawing Sheets

METHOD FOR DETERMINING ELIGIBILITY FOR AN ASSISTANCE PROGRAM

TECHNICAL FIELD

This invention relates in general to the collection and analysis of data, and more particularly to collecting data and analyzing data to determine whether a patient is eligible for benefits under a healthcare assistance program and for facilitating the acquisition of such benefits.

BACKGROUND OF THE INVENTION

When a patient enters a hospital or other medical facility for treatment, the patient is typically asked about health insurance that can be used to pay for the patient's treatment. If the patient is not covered by insurance or covered by a healthcare assistance program, then the patient is deemed to be a self-pay patient. Some self-pay patients are indigent or disabled and may qualify for benefits under a healthcare assistance program, such as Medicaid.

Even though the patient may be eligible for benefits under an assistance program, the patient may not be receiving benefits because the patient has not applied for assistance or has not completed the application process. Typically, the application process requires that one or more forms be completed and submitted. In addition, there may be a requirement for verification of certain information provided on the application.

Typically, medical facilities are focused on treating patients. The facilities have few, if any, resources that can be used to assist patients in obtaining benefits under a medical assistance program. However, if benefits can be obtained for the patient, then the medical facility can be paid for the treatment services that it rendered to the patient. Thus, there is a need for determining whether a patient qualifies for benefits under an assistance program, and if so, for applying for such benefits.

Each assistance program typically requires a specific application form. A single application form cannot be submitted for all possible assistance programs. Therefore, it is impractical to complete the application process for every possible assistance program for every patient. Thus, there is a need to make an initial determination as to whether a patient is likely to qualify for an assistance program and to identify a particular assistance program prior to starting the application process.

Once an assistance program is identified, the application for that assistance program must be completed. If the application form is incomplete or if the application form includes inconsistent answers, then there may be a delay in obtaining coverage or coverage may be denied. Some application forms include questions that are designed to verify the patient's answers and to combat fraud. A patient may, without fraudulent intent, answer these questions differently. If so, then the patient's application may be rejected or returned to the patient for an explanation. Thus, there is a need for guiding an applicant through the application process, so that the application form is completed consistently.

SUMMARY OF THE INVENTION

The present invention meets the needs described above by providing a multi-step process to determine whether a patient is likely to qualify for benefits under an assistance program, and if so, then submitting an application to the assistance program. An assistance program is typically a federal or state program that provides medical or disability benefits.

In one aspect of the invention, an assistance coordinator receives a patient referral. The assistance coordinator can be independent of the medical facility providing treatment to a patient. Alternatively, the assistance coordinator can be associated with the medical facility providing treatment. The patient referral includes initial patient information, such as the patient's date of birth, the members of the patient's household, the patient's medical condition, including pregnancy, and the patient's vocation. The referral may also include information about the patient's available income and financial resources, if such information is available. Based upon the initial patient information, the assistance coordinator determines whether to accept the patient referral. If the assistance coordinator accepts the patient referral, then the assistance coordinator works with the patient to apply for benefits under an assistance program.

The initial patient information is used in one of the steps of the process to make a determination as to whether a patient has a pending application for assistance. If the patient has a pending application, then a follow-up application or an update form is completed and submitted.

In another one of the steps of the process, the initial patient information is compared to a set of well-established criteria. The set of well-established criteria is based on decisions of the relevant courts and agencies establishing that certain criteria meet the eligibility requirements for a particular assistance program. If the initial patient information does not meet one of the well-established criteria, then the patient information is compared to a set of probability models. The set of probability models are based upon the assistance coordinator's past experience in obtaining benefits for patients. Each probability model corresponds to a particular assistance program.

If the initial patient information satisfies one of the well-established criteria or the probability models, then the assistance program that corresponds to the satisfied criteria or model is identified and additional patient information is obtained. The additional patient information typically includes additional details about the patient's income and financial resources, as well as the income and financial resources of the other members of the patient's household. If the additional patient information reveals that a third party (e.g. insurance company) is liable for the patient's medical treatment, then the medical facility providing treatment is informed. Otherwise, all of the patient information is used to complete the application forms for the identified assistance program.

To help ensure that the application forms are completed consistently, a series of prompts is provided. The prompts identify questions that are related to other questions on the application forms so that the assistance coordinator can verify that the related questions are answered consistently. For example, if the patient is applying for both a federal assistance program and a state assistance program, then the application forms for the federal program and the state program typically include questions that are related (i.e. ask for similar information). The prompts identify these related questions so that the application forms can be completed consistently. Once the application forms are completed, the application forms are submitted to the assistance program.

These and other aspects, features and advantages of the present invention may be more clearly understood and appreciated from a review of the following detailed description of the disclosed embodiments and by reference to the appended drawings and claims.

DETAILED DESCRIPTION OF THE INVENTION

The present invention is directed to a method for collecting and analyzing patient information to determine whether the patient is eligible for benefits under an assistance program, and for facilitating the application process for such benefits. Briefly described, the method makes an initial determination as to whether a patient is likely to qualify for benefits under an assistance program based on initial patient data, such as age, other members of the patient's household, medical condition and vocation. In addition, the patient's income and financial resources are also considered, if such information is available. If the initial determination indicates that the patient is likely to qualify for benefits under an assistance program, then additional patient information is collected and the application forms for the assistance program are completed and submitted.

Assistance Coordinator

When a patient enters a hospital or other medical facility, the facility obtains information about the patient as part of its patient admissions process. Typically, the information indicates whether the patient has private medical insurance or is covered by a state or federal assistance program, such as Medicaid. If the patient does not have medical coverage of any kind, then the patient is a "self-pay" patient. Some self-pay patients are indigent and/or disabled and may qualify for benefits under an assistance program. The present invention uses a multi-step process to determine whether a patient is likely to qualify for an assistance program, and if so, to apply for benefits under the assistance program.

Once a patient is identified as a self-pay patient, the hospital refers the patient to an assistance coordinator. In the exemplary embodiment discussed herein the assistance coordinator is an entity that is independent of the medical facility. The assistance coordinator has representatives that visit patients that the medical facility has identified as a self-pay patients. The representatives visit the patients to obtain the information necessary to determine whether it is likely that the patients qualify for benefits under an assistance program. However, in other embodiments, the assistance coordinator can be associated with the hospital. The assistance coordinator makes an initial determination as to whether the patient is likely to qualify for an assistance program. If the initial determination is that the patient is likely to qualify for an assistance program, then the assistance coordinator accepts the referral from the hospital and attempts to obtain assistance for the patient. If assistance is obtained, then the assistance program pays the hospital for the expenses incurred by the patient. In one embodiment, the medical facility pays the independent assistance coordinator a portion of the money received from the assistance program.

Exemplary Operating Environment

Figure 1:
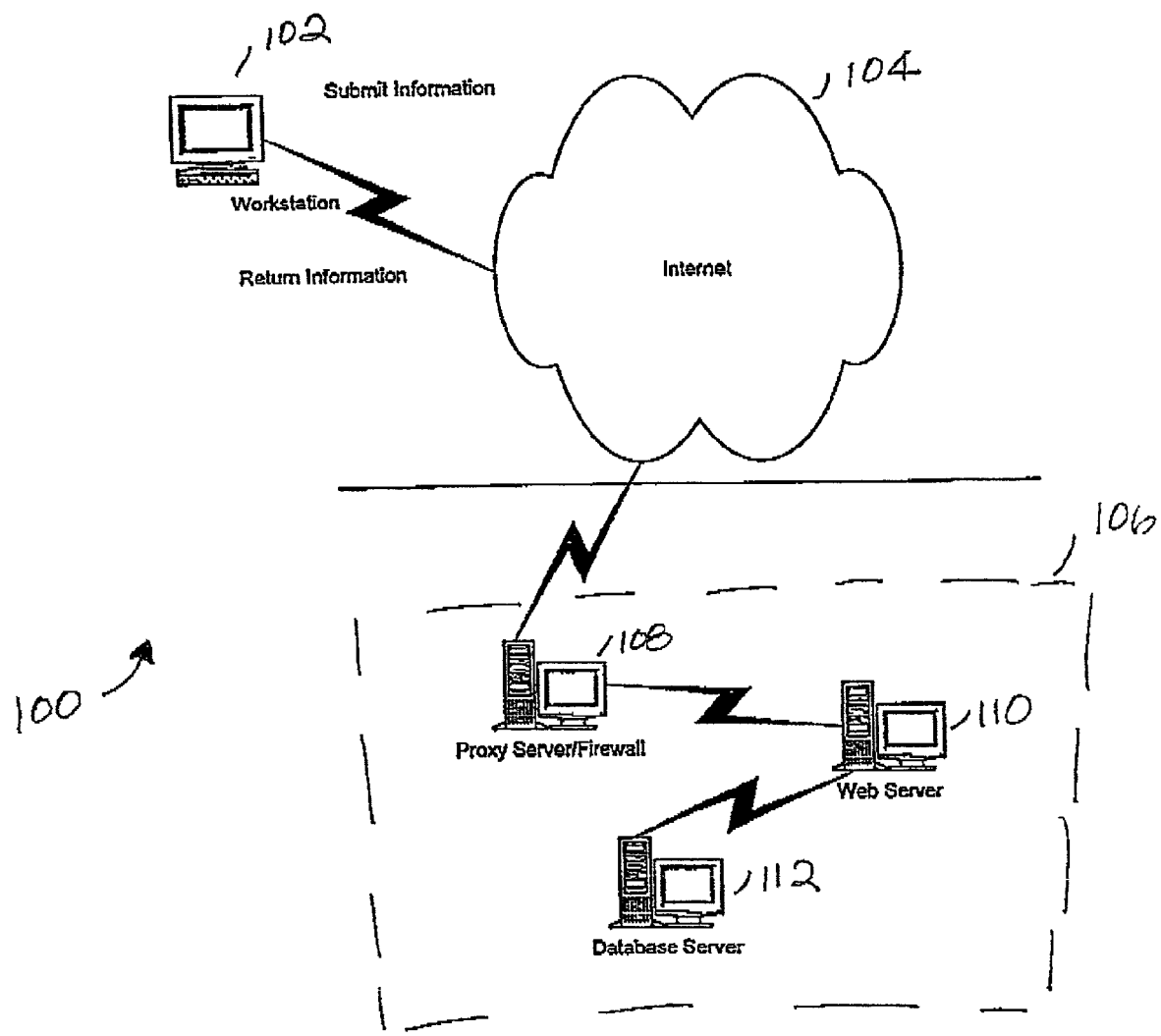
FIG. 1 is a block diagram illustrating an exemplary system, in accordance with an embodiment of the present invention.

FIG. 1 illustrates an exemplary operating environment of the present invention. Although FIG. 1 illustrates an Internet-based system, the system is not limited to the Internet or to a distributed system. Other types of systems can also be used. For example, the system could be implemented using a system that is already in place in a hospital. In the embodiment illustrated by FIG. 1, a distributed system 100 is operated by an assistance coordinator that is independent of the medical facility, such as a hospital, where the patient is being treated. The assistance coordinator uses a workstation 102 to collect patient data. The workstation can be a laptop computer or a portable computer system that can be easily moved between patient rooms. Alternatively, the workstation 102 can be a terminal that is provided by the medical facility. The workstation 102 communicates with a central system 106 using the Internet 104 or other type of communication network.

In FIG. 1, the central system includes a proxy server/firewall system 108, a web server 110 and a database server 112. Other embodiments can use different types or a different number of components in the central system. The proxy server/firewall system 108 interfaces with the Internet 104. The web server 110 communicates with the proxy server/firewall system 108 and provides an Internet-based interface for collecting patient information. The web server supports the eligibility determinations based on the patient data. The web server 110 also communicates with the database server 112. The database server 112 stores the patient data, as well as information about the status of submitted applications. The information stored in the database server 112 can be reviewed to determine how successful the system has been in identifying patients that are likely to qualify for benefits under an assistance program. Based upon the review of the stored information, the probability models used to make a determination as to whether a patient is likely is qualify for assistance can be modified. In addition, if the system supports a number of medical facilities, then all of the information collected from all of the facilities is stored in the database server 112.

The central system can also communicate with other external systems and databases to support eligibility determinations. For example, the central system can communicate with a system or database that provides information on persons that are receiving benefits under a particular assistance program. The central system can also communicate with systems or databases provided by financial institutions and insurance companies to verify a patient's financial resources.

In the embodiment illustrated by FIG. 1, the assistance coordinator receives patient referrals from the medical facility. Typically, the referrals include patients that the medical facility's admission process identified as self-pay patients. The referrals are provided by providing a list of the patients and basic information about the patients. This information is then entered into the workstation 102 and submitted to the central system 106 where the initial determination is made as to whether the patient is likely to qualify for an assistance program. The results of the initial determination are returned to the workstation. Alternatively, the initial determination can be made at the workstation, rather than at the central system. If the initial determination indicates that the patient is likely to qualify for an assistance program, then the assistance coordinator obtains additional information from the patient and enters the information into the workstation 102.

Once the additional information is obtained from the patient, then all of the patient information is evaluated to determine whether it is likely that the patient qualifies for benefits under an assistance program. If it is determined that it is likely that the patient qualifies for benefits under the assistance program, then the application forms for the identified program are completed. The representative completes that application form by obtaining the requested information from the patient and entering the information into the workstation 102. Once the application is complete, a copy of the application is printed and the printed copy of the application is reviewed and signed by the patient. Alternatively, if the assistance program accepts electronic forms, then the application can be reviewed and signed by the patient electronically.

Any other necessary forms or applications are completed in a similar manner. For example, the patient typically executes a form that designates the assistance coordinator as the patient's representative so that the assistance coordinator can check the status of the patient's application and facilitate the processing of the application on behalf of the patient. In addition, if a consent form is needed to verify income or financial resources, then the consent form is also completed. If it appears that the patient may be eligible for multiple assistance programs, then all applications for the identified programs are completed at the same time. Completing all applications and forms that may be relevant to the patient while the patient is in the hospital avoids having to go back to the patient at a later time to obtain additional information. Thus, the problem of locating a patient that may not have a permanent address is avoided.

Alternatively, the workstation used by the assistance coordinator can be connected to the medical facility's system. If so, then the patient information can be easily accessed by the workstation. In yet another embodiment, the activities of the assistance coordinator can be performed by personnel employed by the medical facility.

For the purposes of this discussion, a method or process is generally conceived to be a sequence of computer-executed steps leading to a desired result. These steps generally require physical manipulations of physical quantities. In addition, it should be understood that the methods and systems described herein are not related or limited to any particular computer (standalone or distributed) or apparatus. Furthermore, the methods and systems are not related or limited to any particular communication architecture. Thus, one skilled in the art will be able to implement the systems and methods of the present invention with general purpose machines or specially customized programmable devices according to the teachings described herein.

Eligibility Requirements

Eligibility requirements are defined by an assistance program and determine whether a person is eligible to receive benefits under the assistance program. An assistance program is typically a federal or state program that provides medical benefits. For example, the Temporary Assistance to Needy Families program in Georgia provides assistance to single parents with minor children under the age of 18, if the family meets certain income and financial resource limits. The Medically Needy program in Georgia provides assistance to a person who is under the age of 19 or pregnant. Although there are no income limits for the Medically Needy assistance program, there is a deductible based on the person's income and financial resources.

A set of well-established criteria and a set of probability models are used to make an initial determination as to whether a patient is likely to qualify for an assistance program. The set of well-established criteria is based upon court and agency decisions establishing that certain criteria meet the eligibility requirements for a particular assistance program. For example, if a court determined that a patient of a certain age having vocational experience limited to manual labor and having a particular medical disability was eligible for a disability program, then the factors used by the court can be used to create a criteria.

The probability models are defined by the assistance coordinator and are based on historical information and probability modeling. The historical information includes patient data collected by the assistance coordinator and the results of applications submitted by the assistance coordinator to a particular assistance program. The historical information can also include information that the assistance coordinator has collected from an outside source. The factors typically considered by the probability models include the patient's age, the other members of the patient's household, the patient's monthly income, including sources of income (e.g. whether the source of the income is from a disability check), the patient's assets and other financial resources, the patient's medical condition, including pregnancy, the patient's vocational history, the patient's education level and whether the patient's condition resulted from a crime. A probability model may consider some or all of these factors. For example, a probability model for a disability assistance program typically considers the patient's education level, whereas a probability model for a medical assistance program does not. Moreover, there may be no information initially available about the patient's income or other financial resources. This situation is common where the patient has been admitted to a hospital because the patient required emergency treatment. Additional probability models can be created to accommodate additional assistance programs or an existing probability model can be modified if the eligibility requirements for the program is modified.

If the initial information received from the patient indicates that the patient meets either one of the criteria or the probability models, then the assistance program that corresponds to the well-defined criteria or the probability model is identified and additional information is obtained from the patient. The additional information typically focuses on details of the patient's income and resources. Once all of the patient information is obtained, the information is analyzed to determine whether it is likely that the patient will qualify for benefits under the assistance program. Typically, the information is analyzed to determine whether the patient information indicates that the patient will not qualify for benefits under the assistance program. For example, if the patient's income and/or financial resources exceed a limit for the assistance program, then the determination is that the patient is unlikely to qualify for benefits for that program.

As more and more patient information is collected, the patient information can be analyzed to determine whether it is necessary to adjust any of the probability models. For example, if the collected patient information indicates that if a patient's income is less than a certain amount, then benefits are typically available, regardless of medical condition or other members of the patient's household, then the probability models are reviewed to ensure that this situation is covered. Preferably, the patient information is used anonymously to adjust the probability models, i.e. the information that identifies the patient is not considered.

Exemplary Method for Determining Patient Eligibility

Figure 2A:
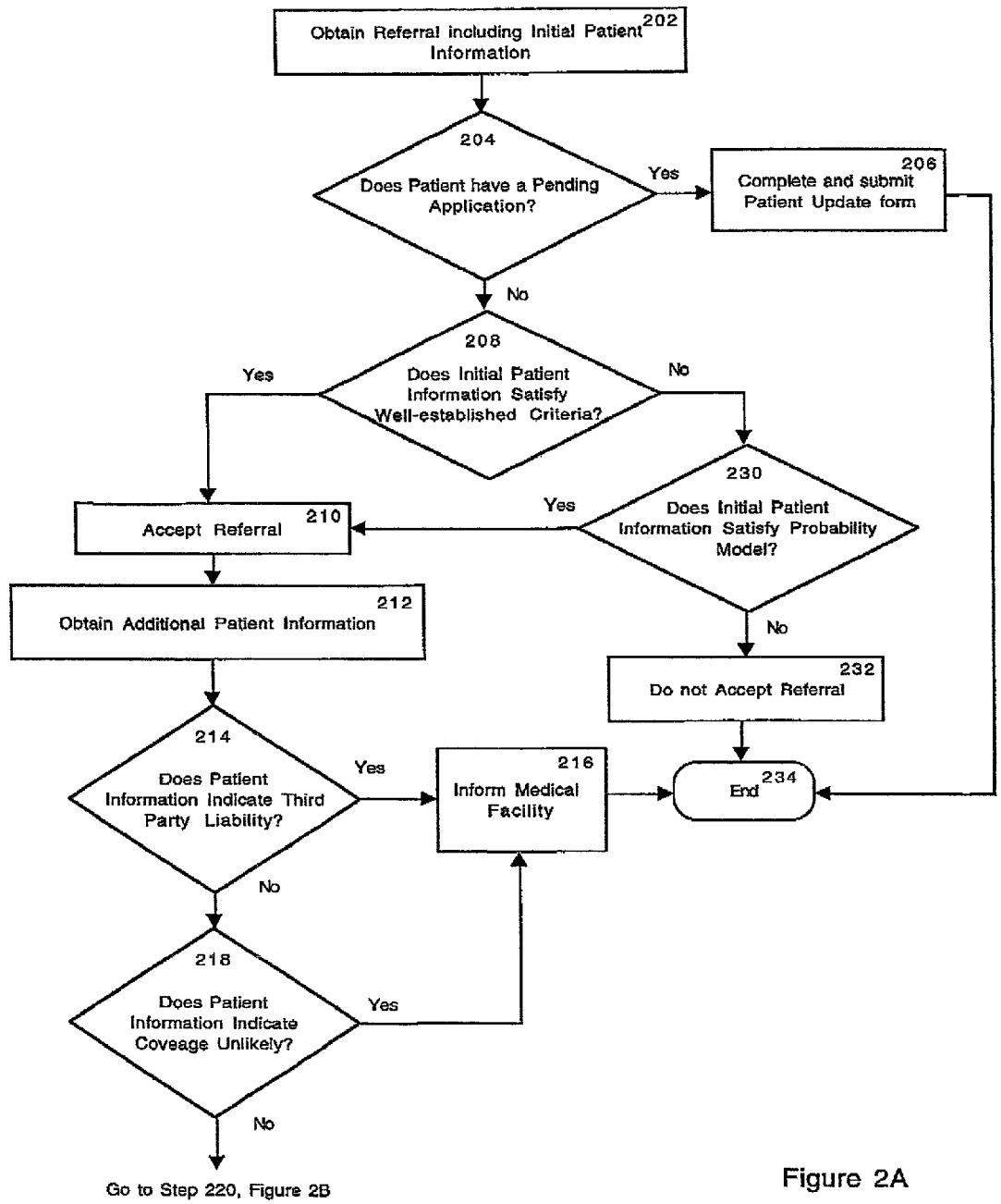
FIG. 2, consisting of FIGS. 2A and 2B, is a flow diagram illustrating an exemplary method for determining eligibility, in accordance with an embodiment of the present information.
Figure 2B:
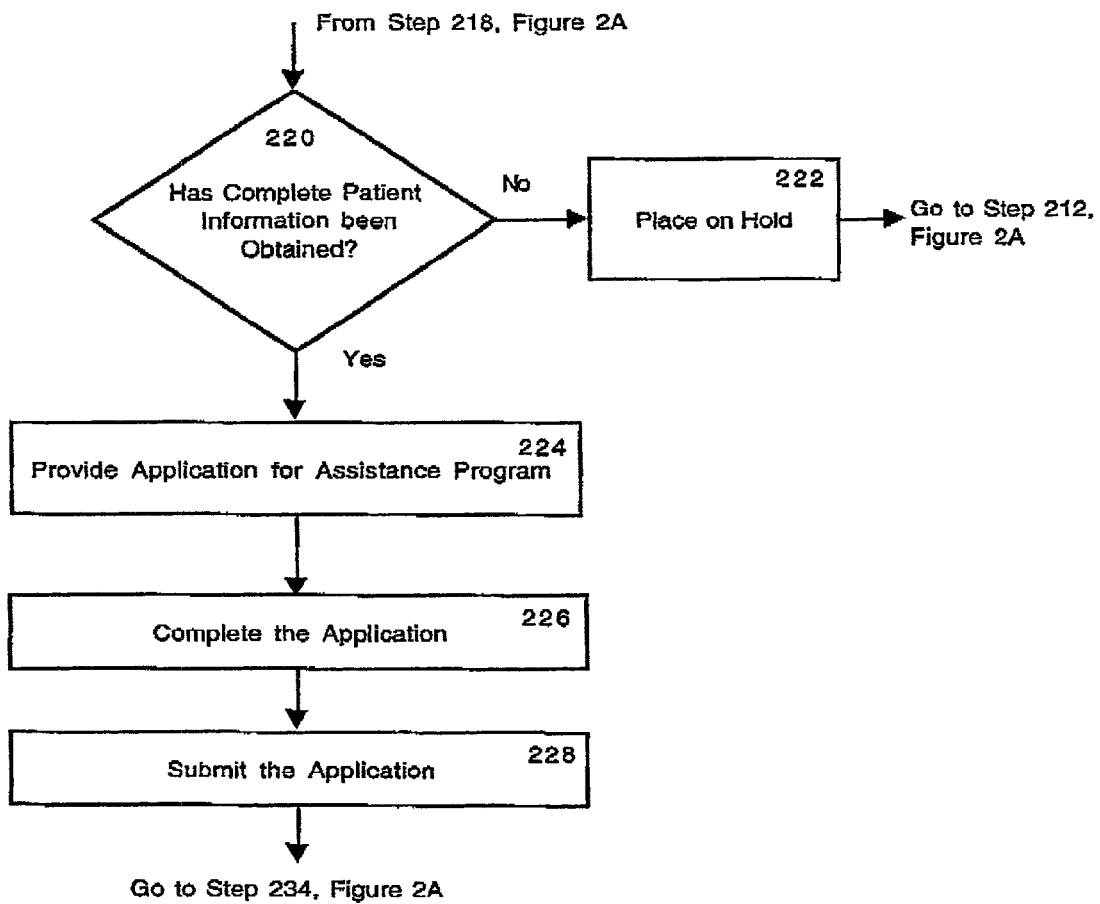

An exemplary method 200 for determining patient eligibility is shown in FIG. 2 which includes FIGS. 2A and 2B. The method begins at step 202 when initial patient information is received. Typically, the initial patient information includes the patient's date of birth, the members of the patient's household, the patient's medical condition, including pregnancy, and the patient's vocation. In some situations the initial patient information also includes the patient's available income and financial resources. The initial patient information can be obtained in connection with the referral of a patient to an assistance coordinator. The initial patient information is used in step 204 to determine whether there is a pending application for the patient. An application may have been submitted on the patient's behalf in connection with a previous admission to the medical facility or in connection with a previous admission to a different medical facility. The assistance coordinator can support a number of medical facilities. Preferably, the patient information collected from all of the facilities is stored in a common database so that the assistance coordinator can determine that an application has previously been submitted for the patient.

If the determination in step 204 is that there is a pending application for the patient, then the Yes branch is followed to step 206. In step 206 a patient update form is completed and submitted. Typically, the patient update form is completed by obtaining some additional information from the patient. Once the patient update form is completed, the method ends at step 234. Although not shown in FIG. 2A, it is also possible that once the patient update form is completed, that the method will proceed to step 208, rather than ending. This situation may occur if the patient's status has changed dramatically. For example, the patient was originally admitted with a non-terminal illness, but the patient is diagnosed with a terminal illness in a subsequent admission. Typically, the representative of the assistance coordinator makes the determination that the patient's condition has changed dramatically.

If the determination in step 204 is that there is no pending application, then the No branch is followed to step 208. In step 208 a determination is made as to whether the initial patient information satisfies the well-established criteria. If the determination is that the initial patient information satisfies one of the well-established criteria, then the Yes branch is followed to step 210 and the referral is accepted. However, if the determination is that the initial patient information does not satisfy one of the well-established criteria, then the No branch is followed to step 230. In step 230 a determination is made as to whether the initial patient information satisfies a probability model. If the determination is that the initial patient information satisfies one of the probability models, then the Yes branch is followed to step 210 and the referral is accepted. However, if the determination is that the initial patient information does not satisfy one of the probability models, then the No branch is followed to step 232 and the referral is rejected. Once the referral is rejected, the method ends at step 234.

If the referral is accepted in step 210, then additional patient information is obtained in step 212. The additional patient information includes additional details about the patient's income and financial resources, as well as the income and financial resources of the other members of the patient's household. Preferably, the additional information is obtained from the patient before the patient leaves the medical facility. In step 214, a determination is made as to whether the additional information indicates that there is third party liability, e.g. insurance coverage for the patient. Although the medical facility should only refer self-pay patients to the assistance coordinator, sometimes a referral is made in error so the assistance coordinator verifies that there is no third party liability. If the determination in step 214 is that there is third party liability, then the Yes branch is followed to step 216 and the medical facility is informed that there is third party liability. The method then ends at step 234.

However, if the determination in step 214 is that the patient information does not indicate that there is third party liability, then the No branch is followed to step 218. In step 218 a determination is made as to whether the patient information indicates that it is unlikely that there is coverage available for the patient. Typically, the determination that it is unlikely that there is coverage available for the patient is made by identifying information that would disqualify a patient for benefits under an assistance program. If the initial patient information satisfied one of the well-established criteria, then the patient information is compared to the requirements for the assistance program that corresponds to the well-established criteria to determine whether the patient is likely to qualify for benefits under the assistance program. For example, if the patient's income and/or financial resources exceed a threshold established by the assistance program, then the determination at step 218 is that coverage is unlikely. If the patient information indicates that it is unlikely that there is coverage available, then the Yes branch is followed to step 216 and the medical facility is informed. Once the medical facility is informed that it is unlikely that there is coverage available, then the method ends at step 232.

If the determination in step 218 is that the patient information does not indicate that it is unlikely that coverage is available, then the No branch is followed to step 220 of FIG. 2B. In step 220, a determination is made as to whether complete patient information has been obtained. The patient information may be incomplete if complete test results are not yet available, if the patient interview has not been completed, or if an interview of a member of the patient's household has not been completed. The information may also be incomplete if a discharge diagnosis has not yet been determined. If complete patient information has not been obtained, then the No branch is followed to step 222 and the method is placed on hold until the needed information becomes available. Once the information becomes available, the method proceeds to step 212 of FIG. 2A.

If the determination in step 220 is that complete patient information has been obtained, then the Yes branch is followed to step 224. Although FIG. 2 shows that determinations in steps 214, 218 and 220 occur sequentially, those skilled in the art will appreciate that the determinations can occur simultaneously, or in an alternative order to that shown in FIGS. 2A and 2B.

In step 224, an application for the assistance program is provided and in step 226 the application is completed. The application corresponds to the well-established criteria or the probability model that was identified in step 208 or step 210. Typically, each assistance program has a unique application, so that a generic application form cannot be used for multiple programs. Typically, the application is provided by displaying the application on the workstation so that the application can be completed on the workstation. In addition, the representative of the assistance coordinator is provided with prompts to assist in the completion of the application. Once the application is completed on the computer, the application is reviewed by the patient and signed. Typically, the application is printed on a printer connected to the workstation and the patient signs the printed application. If the assistance program accepts electronic signatures, then the patient can review and electronically sign the application using the workstation. Once the application is completed, the application is submitted to the assistance program in step 228 and the method ends at step 234.

Although not shown in FIG. 2, if the initial patient information satisfies more than one well-established criteria or probability model, then multiple applications are provided, and steps 224, 226 and 228 are repeated for each assistance program identified.

Completing an Application for an Assistance Program

When an application for an assistance program is provided to the representative of the assistance coordinator, wherever possible, the basic information for the patient is automatically entered into the application. For example, the patient's name and social security number may be required on each page of the application. If so, then the patient's name and social security number are automatically entered on each page of the application. However, many programs require that the patient respond to a question, even if the same or a similar question was previously presented to the patient. Also, there may be similar questions on an application form for a federal program and an application form for a state program. For these types of questions, it is not permissible to copy an answer from a previous question. However, related questions are recognized and a prompt is presented to the representative of the assistance coordinator so that the representative can ensure that the related questions are answered consistently.

For example, an application may ask for the patient's last day at work, as well as the date of the patient's disability. Typically, these two dates should be relatively close in time. To ensure that the dates are close in time, a prompt is presented to the representative when each of these questions is presented so that the representative can verify the dates. Alternatively, the answers to the two questions can be compared automatically and if there is a discrepancy, then the representative can be notified to resolve the discrepancy.

Alternative embodiments will be apparent to those skilled in the art to which the present invention pertains without departing from its spirit and scope. For example, although the present invention has been described in connection with an assistance coordinator that is independent of the medical facility, the present invention is not limited to an independent assistance coordinator. In addition, the present invention is not limited to the assistance programs described herein. Accordingly, the scope of the present invention is described by the appended claims and is supported by the foregoing description.

What is claimed is:

1. A computer-implemented method for identifying and applying for benefits for a patient, comprising the steps of:
    receiving a referral from a medical facility for a patient and receiving initial patient information, at at least one of a workstation and a server;
    based on the initial patient information, the at least one of the workstation and the server making an initial determination as to whether it is likely that benefits can be obtained for the patient under an assistance program;
    if the initial determination is that it is unlikely that benefits can be obtained then rejecting the referral;
    if the initial determination is that it is likely that benefits can be obtained for the patient, then receiving additional patient information, at the at least one of the workstation and the server;
    based on the additional patient information, the at least one of the workstation and the server making a second determination as to whether it is likely that benefits can be obtained for the patient under the assistance program;
    if the second determination is that it is likely that benefits can be obtained, then the at least one of the workstation and the server providing an application for the assistance program; and
    the at least one of the workstation and the server undertaking to perform at least one of submitting a completed application to the assistance program and providing a copy of the completed application for submission to the assistance program.

2. The method of claim 1, wherein the step of receiving the initial patient information includes receiving information about the patient's age and medical condition.

3. The method of claim 1, wherein the step of receiving the initial patient information includes receiving information about the patient's income and financial resources.

4. The method of claim 1, wherein the at least one of the workstation and the server making the initial determination as to whether it is likely that benefits can be obtained for the patient under an assistance program, comprises:
    the at least one of the workstation and the server comparing the initial patient information to a well-established criteria for the assistance program.

5. The method of claim 4, wherein the at least one of the workstation and the server comparing the initial patient information to the well-established criteria for the assistance program includes comparing the initial patient information to well-established criteria that is based upon a court decision.

6. The method of claim 4, wherein the at least one of the workstation and the server comparing the initial patient information to the well-established criteria for the assistance program includes comparing the initial patient information to well-established criteria that is based upon an agency decision.

7. The method of claim 1, wherein the at least one of the workstation and the server making the initial determination as to whether it is likely that benefits can be obtained for the patient under an assistance program, comprises:
    the at least one of the workstation and the server comparing the initial patient information to a probability model.

8. The method of claim 7, wherein the at least one of the workstation and the server comparing the initial patient information to a probability model includes comparing the initial patient information to a probability model that is based upon prior experience in obtaining benefits under the assistance program for a plurality of patients.

9. The method of claim 1, wherein the step of receiving the additional patient information includes receiving a discharge diagnosis.

10. The method of claim 1, wherein the at least one of the workstation and the server providing the application for the assistance program comprises:
    the at least one of the workstation and the server providing prompts to assist in completion of the application.

11. The method of claim 1, further comprising:
    the at least one of the workstation and the server determining whether the patient is already covered by an assistance program.

12. The method of claim 1, further comprising:
    the at least one of the workstation and the server determining whether the patient has previously submitted a first application for a first assistance program;
    if the patient has previously submitted a first application for a first assistance program, then the at least one of the workstation and the server determining the status of the first application; and
    if the status of the first application is pending, then the at least one of the workstation and the server providing an update for the first application.

13. A computer-implemented method for accepting a patient referral for Medicaid, comprising the steps of:
    receiving a patient referral at at least one of a workstation and a server, the patient referral including initial patient information;
    the at least one of the workstation and the server determining whether to accept the patient referral by: comparing the initial patient information to a well-established criteria associated with a Medicaid first assistance program;
    if the comparison indicates that the initial patient information satisfies the well-established criteria, then accepting the patient referral;
    if the patient referral is accepted, then receiving additional patient information, at the at least one of the workstation and the server;

the at least one of the workstation and the server comparing the initial patient information and the additional patient information to eligibility requirements for the Medicaid first assistance program; and if the comparison indicates it is likely that benefits can be obtained under the Medicaid first assistance program, then the at least one of the workstation and the server providing an application for the Medicaid first assistance program.

14. The method of claim 13, wherein the at least one of the workstation and the server determining whether to accept the patient referral further comprises:

the at least one of the workstation and the server comparing the initial patient information to a probability model associated with a second assistance program;

if the comparison indicates that the initial patient information satisfies the probability model, then accepting the patient referral.

15. The method of claim 14, wherein the at least one of the workstation and the server comparing the initial patient information to the probability model associated with the second assistance program includes comparing the initial patient information to a probability model that is based upon prior experience in obtaining benefits under the second assistance program for a plurality of patients.

16. The method of claim 14, wherein the at least one of the workstation and the server comparing the initial patient information to the probability model associated with the second assistance program includes comparing the initial patient information to a probability model that is modified based upon actual experience in obtaining benefits under the second assistance program.

17. The method of claim 13, wherein the at least one of the workstation and the server providing the application for the first assistance program, comprises:

the at least one of the workstation and the server providing prompts during completion of the application to ensure the application is answered consistently.

18. The method of claim 13, wherein the at least one of the workstation and the server providing the application for the first assistance program, comprises:

the at least one of the workstation and the server automatically completing a section of the application using the initial patient information.

19. The method of claim 13, wherein the steps of receiving and accepting the patient referral include receiving and accepting the patient referral by an entity that is independent of a medical provider providing treatment to the patient.

20. The method of claim 19, wherein the step of accepting the patient referral, further comprises a step of determining if payment is provided to a medical provider providing treatment to the patient by the assistance program, and if so then paying the entity a portion of the payment from the medical provider.

21. The method of claim 13, further comprising:

the at least one of the workstation and the server submitting the application; and the at least one of the workstation and the server monitoring the application.

22. The method of claim 13 wherein the step of comparing the initial patient information to the well-established criteria associated with the Medicaid first assistance program includes analyzing the patient's disability status.

23. The method of claim 13 wherein the step of comparing the initial patient information to the well-established criteria associated with the Medicaid first assistance program includes analyzing the patient's indigence status.

24. A computer-implemented method for selecting an assistance program for a patient, comprising the steps of:

receiving initial patient information, at at least one of a workstation and a server;

based on the initial patient information, the at least one of the workstation and the server making an initial determination as to whether it is likely that benefits can be obtained for the patient under an assistance program by:

the at least one of the workstation and the server comparing the initial patient information to a well-defined criteria corresponding to a first assistance program;

if the initial patient information satisfies the well-defined criteria, then the at least one of the workstation and the server identifying the first assistance program;

the at least one of the workstation and the server comparing the initial patient information to a probability model corresponding to a second assistance program;

if the initial patient information satisfies the probability model, then the at least one of the workstation and the server identifying the second assistance program;

if the initial determination is that it is likely that benefits can be obtained, then receiving additional patient information, at the at least one of the workstation and the server;

the at least one of the workstation and the server making a subsequent determination as to whether it is likely that benefits can be obtained for the patient by comparing the initial patient information and the additional patient information to the first and second identified assistance programs that are identified; and if the subsequent determination is that it is likely that benefits can be obtained for the patient, then selecting the identified assistance program.

25. The method of claim 24, further comprising:

the at least one of the workstation and the server identifying an application for the selected assistance program; and the at least one of the workstation and the server providing prompts to assist in the completion of the application, the prompts identifying related questions.

26. The method of claim 24, wherein the step of receiving the initial patient information includes receiving an age and a medical condition.

27. The method of claim 24, wherein the step of receiving additional patient information includes receiving income and financial resource information for member's of the patient's household.

28. The method of claim 24, wherein the at least one of the workstation and the server comparing the initial patient information to the well-defined criteria corresponding to the first assistance program includes comparing the initial patient information to well-defined criteria that is based upon a judicial determination of eligibility under the first assistance program.

29. The method of claim 24, wherein the at least one of the workstation and the server comparing the initial patient information to the probability model corresponding to the second assistance program includes comparing the initial patient information to a probability model that is based upon prior experience in obtaining benefits under the second assistance program for a plurality of patients.

30. The method of claim 29, further comprising:

adjusting the probability model based upon common characteristics shared by a plurality of patients that did not receive benefits under the second assistance program.

* * * * *